United States Patent
Ohishi

(10) Patent No.: US 11,752,362 B2
(45) Date of Patent: Sep. 12, 2023

(54) RADIOTHERAPY PLANNING APPARATUS, RADIOTHERAPY APPARATUS, AND RADIOTHERAPY PLANNING METHOD

(71) Applicant: Toshiba Medical Systems Corporation, Otawara (JP)

(72) Inventor: Satoru Ohishi, Otawara (JP)

(73) Assignee: Canon Medical Systems Corporation, Otawara (JP)

(*) Notice: Subject to any disclaimer, the term of this patent is extended or adjusted under 35 U.S.C. 154(b) by 381 days.

(21) Appl. No.: 15/648,962

(22) Filed: Jul. 13, 2017

(65) Prior Publication Data

US 2018/0015304 A1 Jan. 18, 2018

(30) Foreign Application Priority Data

Jul. 14, 2016 (JP) .................................. 2016-139396

(51) Int. Cl.
*A61N 5/10* (2006.01)

(52) U.S. Cl.
CPC ......... *A61N 5/1039* (2013.01); *A61N 5/1044* (2013.01); *A61N 5/1049* (2013.01); *A61N 5/1081* (2013.01); *A61N 2005/1052* (2013.01); *A61N 2005/1055* (2013.01); *A61N 2005/1061* (2013.01); *A61N 2005/1087* (2013.01)

(58) Field of Classification Search
CPC .. A61N 5/103–1084; A61N 2005/1032–1098; H05H 2007/002; H05H 2007/004; H05H 2007/007; H05H 7/00–22; H05H 9/00–048; H05H 13/00–10
See application file for complete search history.

(56) References Cited

U.S. PATENT DOCUMENTS

| | | | | |
|---|---|---|---|---|
| 2004/0200983 A1* | 10/2004 | Fujimaki | ................. | A61N 5/10 250/492.3 |
| 2006/0153330 A1* | 7/2006 | Wong | ................. | A61B 6/4233 378/65 |
| 2010/0086183 A1* | 4/2010 | Vik | ................. | A61N 5/1031 382/128 |
| 2010/0219356 A1* | 9/2010 | Bzdusek | ................. | A61N 5/103 250/492.1 |
| 2012/0136194 A1* | 5/2012 | Zhang | ................. | A61N 5/103 600/1 |
| 2013/0287170 A1* | 10/2013 | Ebstein | ................. | G01N 23/04 378/62 |
| 2015/0273241 A1 | 10/2015 | Ito et al. | | |

FOREIGN PATENT DOCUMENTS

| | | |
|---|---|---|
| JP | 7-255867 | 10/1995 |
| JP | 2006-87649 | 4/2006 |
| JP | 2015-186536 | 10/2015 |

* cited by examiner

*Primary Examiner* — Kaylee R Wilson
(74) *Attorney, Agent, or Firm* — Oblon, McClelland, Maier & Neustadt, L.L.P.

(57) ABSTRACT

According to one embodiment, a radiotherapy planning apparatus includes processing circuitry. The processing circuitry calculates initial irradiation directions of particle beams and an initial dose distribution corresponding to the initial irradiation directions by using a three-dimensional medical image concerning an object. The processing circuitry disperses some or all of the initial irradiation directions in response to a dispersion instruction via an input device. The processing circuitry modifies the initial dose distribution based on the dispersed irradiation directions.

24 Claims, 9 Drawing Sheets

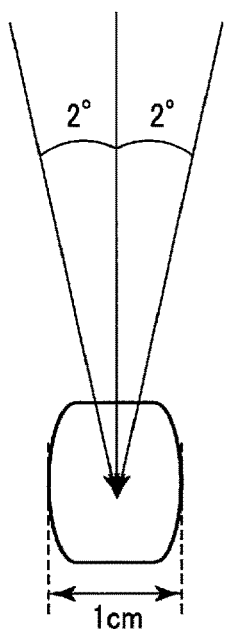
F I G. 10
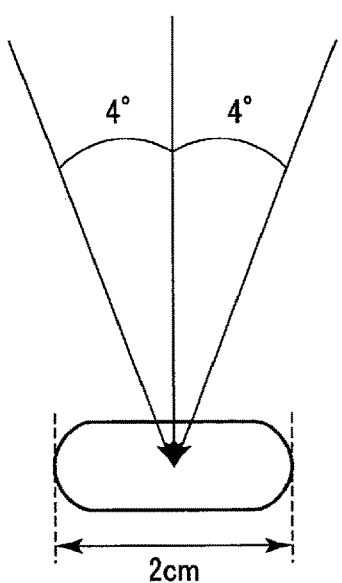
F I G. 11

| | Irradiation direction | Repainting count | |
|---|---|---|---|
| C1 ☐ | 0 | 4 | 12 |
| ☒ | 90 | 4 | |
| ☐ | | | |
| ☐ | | | |

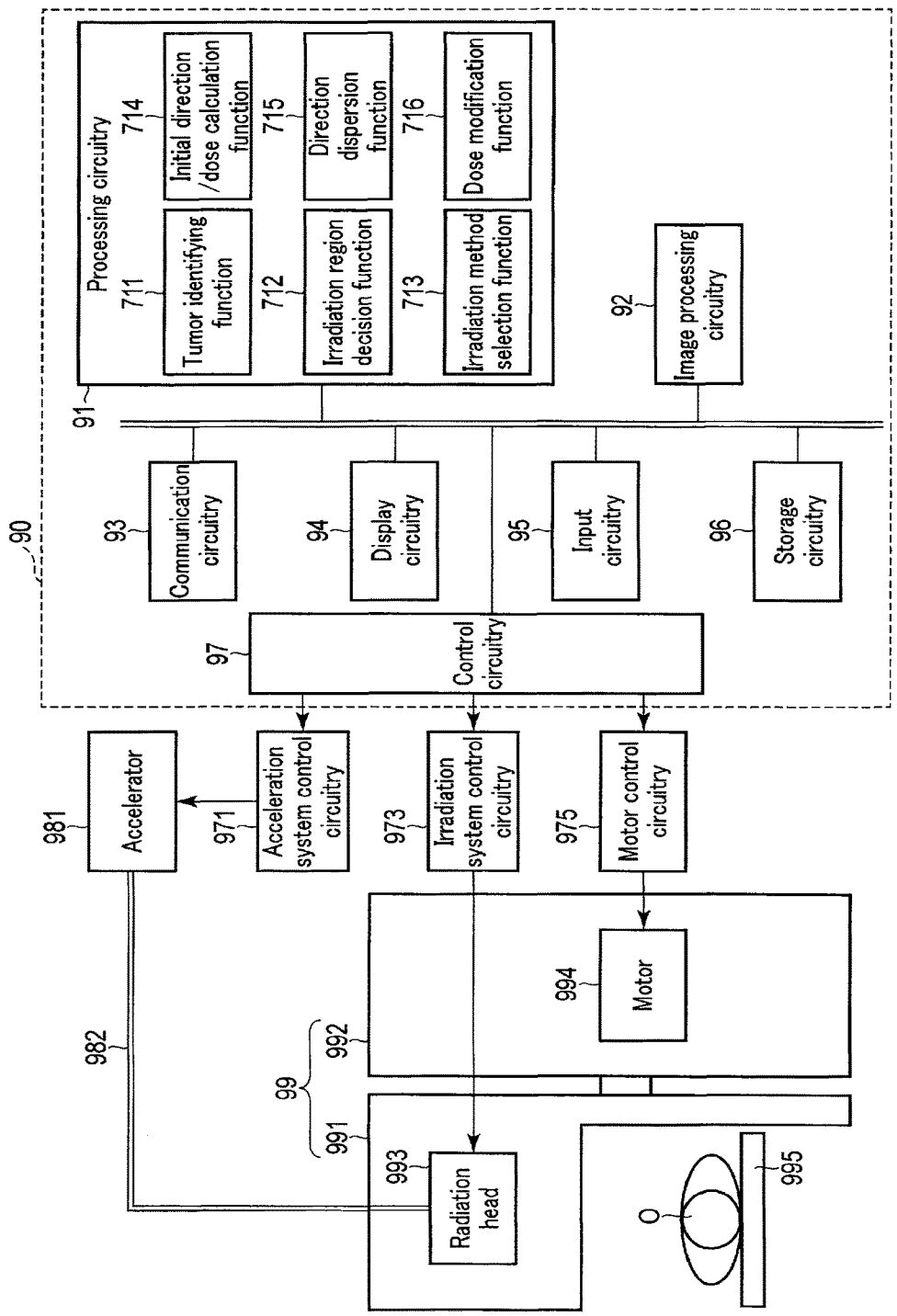
F I G. 14

RADIOTHERAPY PLANNING APPARATUS, RADIOTHERAPY APPARATUS, AND RADIOTHERAPY PLANNING METHOD

CROSS-REFERENCE TO RELATED APPLICATIONS

This application is based upon and claims the benefit of priority from the prior Japanese Patent Application No. 2016-139396, filed Jul. 14, 2016 the entire contents of which are incorporated herein by reference.

FIELD

Embodiments described herein relate generally to a radiotherapy planning apparatus, a radiotherapy apparatus, and a radiotherapy planning method.

BACKGROUND

Studies have been made on radiotherapy using heavy-ion beams and proton beams. A particle beam is a generic term of a proton beam and a heavy-ion beam. Radiotherapy using particle beams includes a technique called repainting. Repainting is to average irradiation dose distribution errors due to the body motion of a patient by applying a particle beam in the same irradiation direction a plurality of number of times. In, for example, irradiating a 1 cm×1 cm×1 cm tumor with 2Gy particle beams, irradiation of the entire tumor with 0.5 Gy per beam is repeated four times. When the target tumor moves due to, for example, the body motion of the patient, one particle beam irradiation will lead to distorted dose distribution in an irradiation region. In contrast, repeating particle beam irradiation a plurality of number of times will lead to a flat dose distribution upon averaging of errors.

Particle beam therapy features concentrating a dose on only a tumor by the Bragg peak. The Bragg peak can be spread out by applying a particle beam in the same irradiation direction while changing depth of the Bragg peak. When a Spread-out Bragg peak is formed by using proton beams, the dose on the front side of a target tumor sometimes reaches 80% of the peak. In contrast, it is known that when a Spread-out Bragg peak is formed by using heavy-ion beams, a dose also leaks onto the rear side of the peak. When a Spread-out Bragg peak is formed in this manner, the dose on a normal tissue on the front or rear side of a target tumor sometimes becomes high.

BRIEF DESCRIPTION OF THE DRAWING

FIG. 10 is a view showing the relationship between angular intervals and the size of a tumor region in the rotating direction according to this embodiment;

FIG. 11 is another view showing the relationship between angular intervals and the size of a tumor region in the rotating direction according to this embodiment;

FIG. 14 is a block diagram showing the arrangement of a radiotherapy apparatus according to a modification of this embodiment.

DETAILED DESCRIPTION

A radiotherapy apparatus according to this embodiment includes processing circuitry. The processing circuitry calculates the initial irradiation directions of particle beams and a dose distribution corresponding to the initial irradiation directions by using a three-dimensional medical image concerning an object. The processing circuitry disperses some or all of the initial irradiation directions in response to the issuance of a dispersion instruction via an input device. The processing circuitry modifies the dose distribution based on the dispersed irradiation directions.

The radiotherapy planning apparatus, the radiotherapy apparatus, and the radiotherapy planning method according to this embodiment will be described below with reference to the accompanying drawings.

Figure 1:
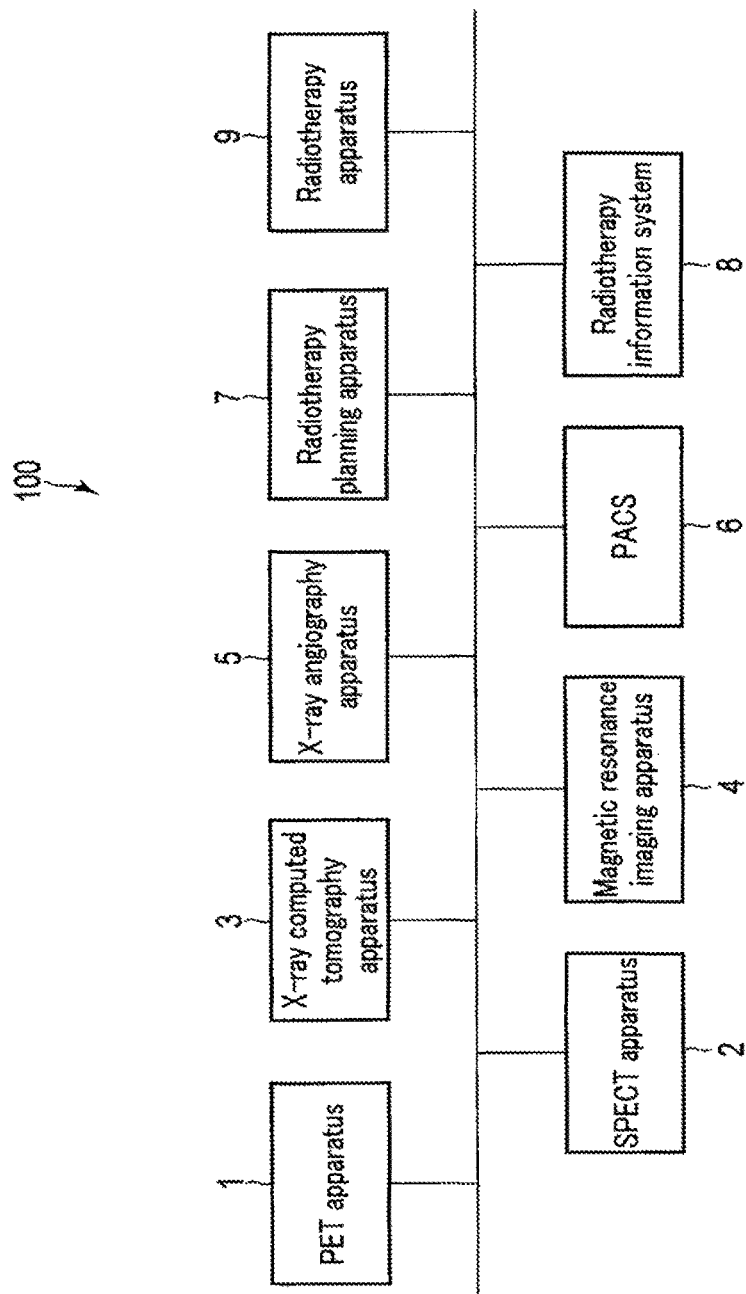
FIG. 1 is a block diagram showing the arrangement of a radiotherapy system including a radiotherapy planning apparatus according to an embodiment.

FIG. 1 shows the arrangement of a radiotherapy system 100 including a radiotherapy planning apparatus 7 according to this embodiment. As shown in FIG. 1, the radiotherapy system 100 includes a PET (Positron Emission Tomography) apparatus 1, a SPECT (Single Photon Emission CT) apparatus 2, an X-ray computed tomography apparatus 3, a magnetic resonance imaging apparatus 4, an X-ray angiography apparatus 5, a PACS (Picture Archiving and Communication System) 6, the radiotherapy planning apparatus 7, a radiotherapy information system 8, and a radiotherapy apparatus 9, which are connected to each other via a network.

The PET apparatus 1, the SPECT apparatus 2, the X-ray computed tomography apparatus 3, the magnetic resonance imaging apparatus 4, and the X-ray angiography apparatus 5 are medical modalities which generate three-dimensional medical images concerning a patient.

The PET apparatus 1 counts a pair of 512-keV gamma rays generated upon pair annihilation of each of positrons generated from radionuclides accumulated in a patient and a corresponding one of electrons existing around the radionuclides by using coincidence circuitry, thereby generating a three-dimensional PET image expressing the spatial distribution of the radionuclides based on coincidence count signals from the coincidence circuitry.

The SPECT apparatus 2 detects single photon gamma rays generated from radionuclides accumulated in an object by using a radiation detector to generate a three-dimensional SPECT image expressing the spatial distribution of the radionuclides based on the detection signals from the radiation detector.

The X-ray computed tomography apparatus 3 radiates X-rays from an X-ray tube while rotating a rotating frame holding the X-ray tube and an X-ray detector at high speed, and detects the X-rays transmitted through a patient using the X-ray detector. The X-ray computed tomography apparatus then generates a three-dimensional CT image expressing the spatial distribution of X-ray attenuation coefficients of substances on the X-ray transmission path based on raw data from the X-ray detector.

The magnetic resonance imaging apparatus 4 applies, for example, RF pulses from an RF coil to excite target atomic nuclei existing in the patient placed in a static magnetic field, and acquires MR signals generated from the target atomic nuclei using the RF coil. The magnetic resonance imaging apparatus 4 then generates a three-dimensional MR image expressing the spatial distribution of the target atomic nuclei based on the MR signals from the RF coil.

The X-ray angiography apparatus 5 radiates X-rays from an X-ray tube while rotating a C-arm holding the X-ray tube and an X-ray detector around the rotation axis, and detects the X-rays transmitted through a patient by using the X-ray detector (CT-like imaging). The X-ray angiography apparatus 5 then generates a three-dimensional X-ray image expressing the spatial distribution of the X-ray attenuation coefficients of substances on the X-ray transmission path based on raw data from the X-ray detector.

The PACS 6 is an image server which manages medical images. For example, the PACS 6 stores three-dimensional PET images from the PET apparatus 1, three-dimensional SPECT images from the SPECT apparatus 2, three-dimensional CT images from the X-ray computed tomography apparatus 3, three-dimensional MR images from the magnetic resonance imaging apparatus 4, and three-dimensional X-ray images from the X-ray angiography apparatus 5. Three-dimensional PET images, three-dimensional SPECT images, three-dimensional CT images, three-dimensional MR images, and three-dimensional X-ray images will be generically termed three-dimensional medical images hereinafter. A three-dimensional medical image is image data constituted by a plurality of voxels arranged three-dimensionally.

The radiotherapy planning apparatus 7 is a computer which produces a radiotherapy plan for the patient by using three-dimensional medical images. The radiotherapy plan information is transmitted to the radiotherapy information system 8.

The radiotherapy information system 8 is an information system which manages radiotherapy schedule information, radiotherapy plan information, medical images, and the like. As the radiotherapy information system 8, for example, an OIS (Oncology Information System) is known. The radiotherapy information system 8 transmits radiotherapy plan information to the radiotherapy apparatus 9.

The radiotherapy apparatus 9 is an apparatus which treats a patient by irradiating a target tumor or the like in the patient with particle beams in accordance with a radiotherapy plan.

Figure 2:
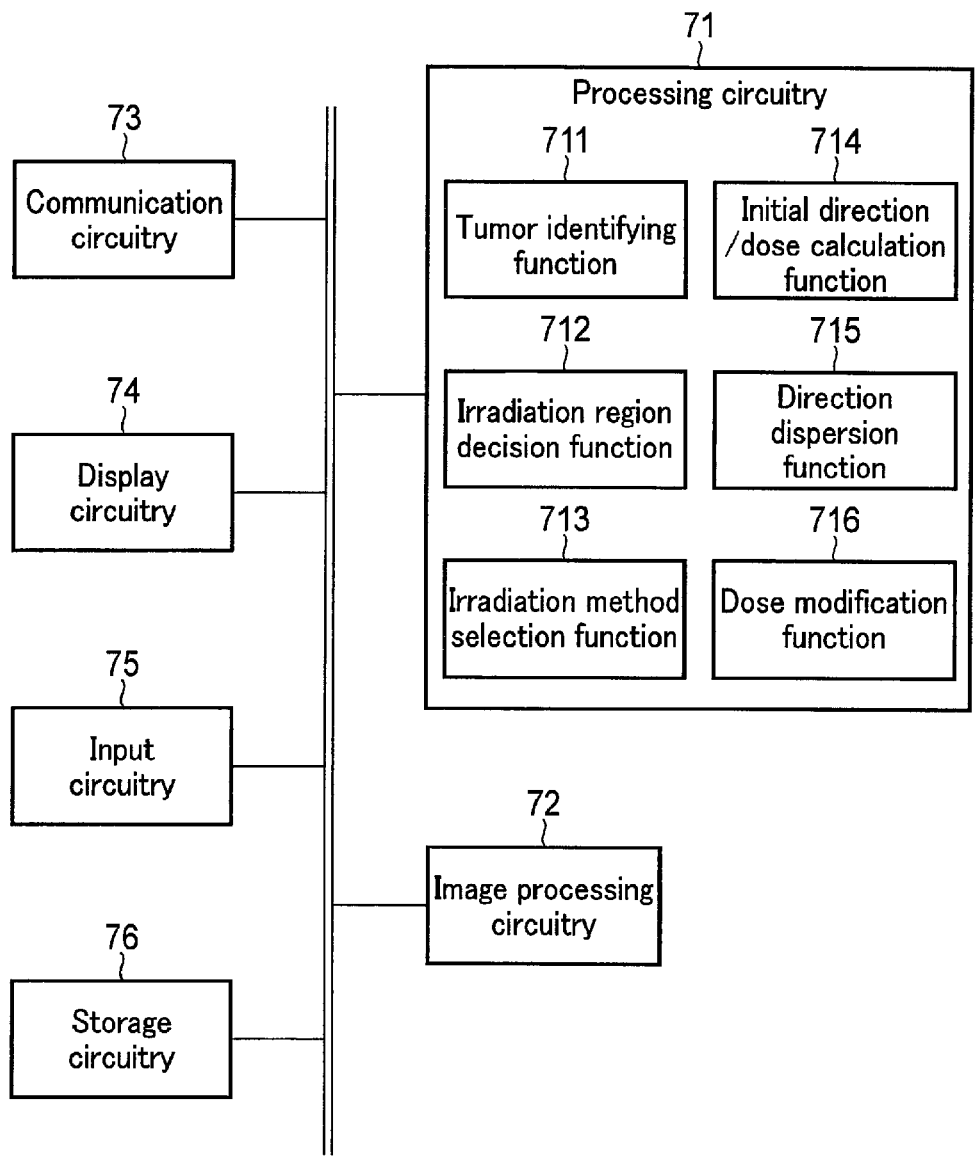
FIG. 2 is a block diagram showing the arrangement of the radiotherapy planning apparatus in FIG. 1.

FIG. 2 shows the arrangement of the radiotherapy planning apparatus 7 in FIG. 1. As shown in FIG. 2, the radiotherapy planning apparatus 7 includes processing circuitry 71, image processing circuitry 72, communication circuitry 73, display circuitry 74, input circuitry 75, and storage circuitry 76. The processing circuitry 71, the image processing circuitry 72, the communication circuitry 73, the display circuitry 74, the input circuitry 75, and the storage circuitry 76 are communicably connected to each other via a bus.

The processing circuitry 71 includes, as hardware resources, a processor such as a CPU (Central Processing Unit) or GPU (Graphics Processing Unit) and memories such as a ROM (Read Only Memory) and a RAM (Random Access Memory). The processing circuitry 71 executes a program concerning a radiotherapy plan (to be referred to as a radiotherapy plan program hereinafter). The radiotherapy apparatus 9 produces a radiotherapy plan concerning a tumors as a particle beam treatment target, and generates radiotherapy plan information including an irradiation region, an irradiation method, a dose distribution, and irradiation directions. When producing a radiotherapy plan, the processing circuitry 71 according to this embodiment executes a tumor identifying function 711, an irradiation region decision function 712, an irradiation method selection function 713, an initial direction/dose calculation function 714, a direction dispersion function 715, and a dose modification function 716.

With the tumor identifying function 711, the processing circuitry 71 identifies an image region (to be referred to as a tumor region hereinafter) concerning a tumor included in a three-dimensional medical image concerning a patient.

With the irradiation region decision function 712, the processing circuitry 71 decides an image region (to be referred to as an irradiation region hereinafter) concerning a particle beam irradiation target based on a tumor region and a predetermined margin.

With the irradiation method selection function 713, the processing circuitry 71 selects a particle beam irradiation method. As an irradiation method, for example, there is available a method designed to select between performing and not performing repainting.

With the initial direction/dose calculation function 714, the processing circuitry 71 calculates the initial irradiation directions of particle beams and a dose distribution corresponding to the initial irradiation directions by using a three-dimensional medical image.

With the direction dispersion function 715, the processing circuitry 71 disperses initial irradiation directions in response to a dispersion instruction via the input circuitry 75. More specifically, the processing circuitry 71 disperses the initial irradiation directions to separate initial irradiation directions from each other by a predetermined angle.

With the dose modification function 716, the processing circuitry 71 modifies the dose distribution calculated by the initial direction/dose calculation function 714 based on the dispersed irradiation directions.

The image processing circuitry 72 includes, as hardware resources, a processor such as a CPU, GPU, or MPU and memories such as a ROM and a RAM. The image processing circuitry 72 applies various types of image processing to three-dimensional medical images. For example, the image processing circuitry 72 generates two-dimensional medical images for display by applying three-dimensional medical image processing such as volume rendering, surface volume rendering, image value projection processing, MPR (Multi-Planar Reconstruction) processing, and CPR (Curved MPR) processing to three-dimensional medical images. Note that the image processing circuitry 72 may be implemented by an ASIC (Application Specific Integrated Circuit), FPGA (Field Programmable Logic Device), CPLD (Complex Programmable Logic Device), or SPLD (Simple Programmable Logic Device) which can implement the above image processing.

The communication circuitry 73 performs data communication with the PET apparatus 1, the SPECT apparatus 2, the X-ray computed tomography apparatus 3, the magnetic resonance imaging apparatus 4, the X-ray angiography apparatus 5, the PACS 6, the radiotherapy information system 8, and the radiotherapy apparatus 9, which constitute the radiotherapy system 100, via a wired or wireless means (not shown).

The display circuitry 74 displays display screens and medical images for radiotherapy planning. More specifically, the display circuitry 74 includes a display interface and a display device. The display interface converts data representing a display target into a video signal. The video image is supplied to the display device. The display device displays the video signal representing the display target. As a display device, it is possible to use, for example, a CRT display, liquid crystal display, organic EL display, LED display, plasma display, or arbitrary display known in this technical field.

More specifically, the input circuitry 75 includes an input device and an input interface. The input device accepts various types of commands from the user. As input devices, it is possible to use a keyboard, mouse, various types of switches, and the like. The input interface supplies output signals from the input device to the processing circuitry 71 and the image processing circuitry 72 via a bus.

The storage circuitry 76 is a storage such as an HDD (Hard Disk Drive), SSD (Solid State Drive), or integrated circuit storage which stores various types of information. Alternatively, the storage circuitry 76 may be a drive assembly or the like which reads and writes various types of information from and to portable storage media such as a CD-ROM drive, DVD drive, and flash memory.

Figure 3:
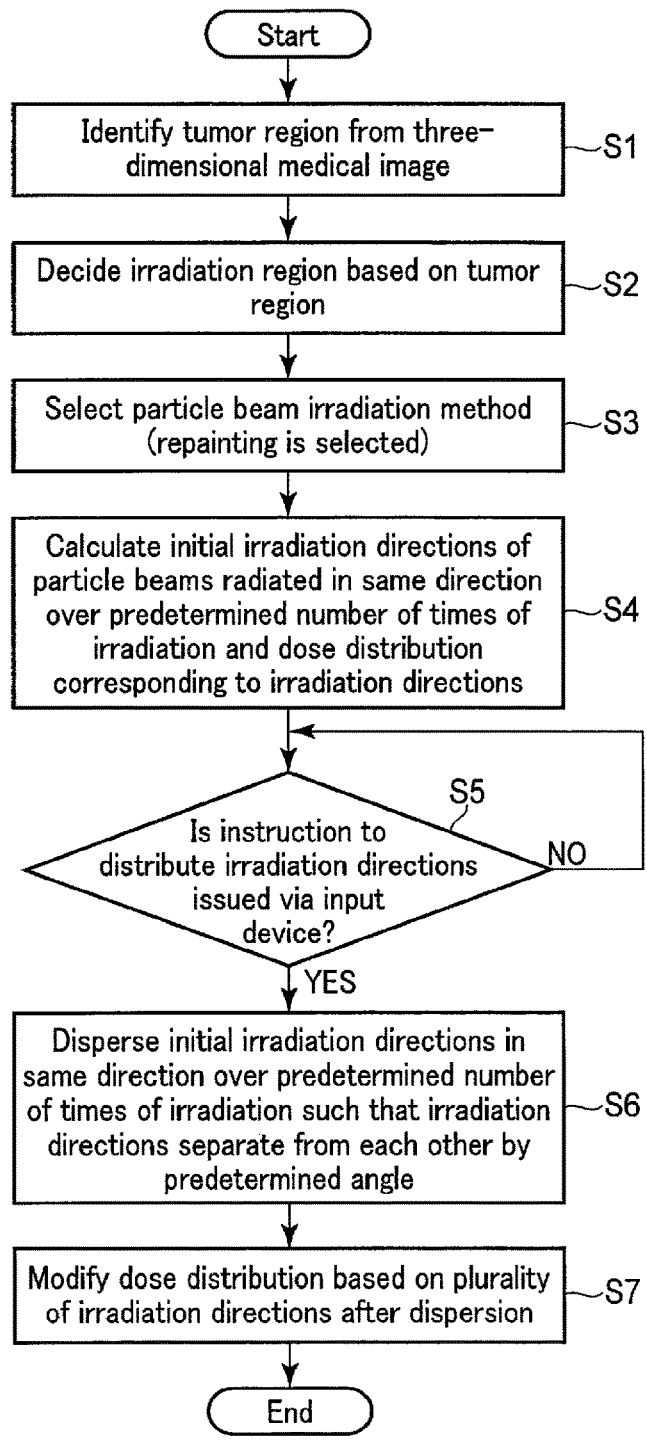
FIG. 3 is a flowchart showing a typical procedure for radiotherapy planning implemented by causing processing circuitry in FIG. 1 to execute a radiotherapy planning program.

An example of the operation of the radiotherapy planning apparatus 7 according to this embodiment will be described below. FIG. 3 is a flowchart showing a typical procedure for radiotherapy planning implemented by causing the processing circuitry 71 to execute a radiotherapy planning program.

As shown in FIG. 3, when radiotherapy planning starts, the processing circuitry 71 executes the tumor identifying function 711 (step S1). In step S1, the processing circuitry 71 identifies a tumor region included in a three-dimensional medical image concerning a patient in accordance with image processing or a user's instruction via the input circuitry 75. When identifying a tumor region by manual determination or by image processing, for example, the processing circuitry 71 uses an existing method such as threshold processing or region growing processing and so on.

Upon executing step S1, the processing circuitry 71 executes the irradiation region decision function 712 (step S2). In step S2, the processing circuitry 71 decides an irradiation region based on the tumor region and a predetermined margin. More specifically, the predetermined margin includes a range in which a tumor can develop, a margin considering a positional shift caused by body motion or the like, and a margin considering an irradiation setting error. The processing circuitry 71 decides, as an irradiation region, an image region including the tumor region and the margin. The user can manually adjust the size of the margin via, for example, the input circuitry 75.

Upon executing step S2, the processing circuitry 71 executes the irradiation method selection function 713 (step S3). In step S3, the processing circuitry 71 selects a particle beam irradiation method. As irradiation methods, BBS (Broad Beam Scan) and PBS (Pencil Beam Scan) are available. BBS is a method of irradiating an irradiation region with a particle beam formed in conformity with the shape of the irradiation region. PBS is a method of repeatedly irradiating an irradiation region with a particle beam formed into a relatively thin shape so as to entirely apply the beam to the region. It is possible to select either BBS or PBS in accordance with the specifications of the radiotherapy apparatus 9. Alternatively, the user may arbitrarily select one of them via the input circuitry 75.

In step S3, the processing circuitry 71 further selects the number of beams as an irradiation method. The number of beams can be decided in accordance with the type of organ having a tumor and the position of the tumor in the organ. For this purpose, the processing circuitry 71 may store a look up table associating the number of beams with each combination of the type of organ having a tumor and the position of the tumor in the organ. In this case, the processing circuitry 71 searches the table by using, as a key, a combination of the type of organ having an tumor and the position of the tumor in the organ, and specifies the number of beams associated with the combination. Note that the number of beams may be set in advance or may be arbitrarily selected by the user via the input circuitry 75.

In step S3, the processing circuitry 71 selects between performing and not performing repainting as in the irradiation method. Repainting is an irradiation method of averaging irradiation dose distribution errors due to the body motion of a patient by applying a particle beam in the same irradiation direction a plurality of number of times. Repainting can be applied to both BBS and PBS. Assume that in this operation example, repainting is selected. When selecting repainting, the processing circuitry 71 also selects a repetitive irradiation count in each irradiation direction. The repetitive irradiation count may be set to more than two and less than 9, preferably more than 2 and less than 6.

An irradiation direction according to this embodiment is defined by the rotation angle of a particle beam radiation head included in the radiotherapy apparatus. The rotation angle of the radiation head is defined by the angle of a gantry equipped with the radiation head around the rotation axis.

Upon executing step S3, the processing circuitry 71 executes the initial direction/dose calculation function 714 (step S4). In step S4, the processing circuitry 71 calculates the initial irradiation directions of particle beams and an initial dose distribution corresponding to the initial irradiation directions by using a three-dimensional medical image. For example, the processing circuitry 71 calculates initial irradiation directions with respect to the respective fields based on radiotherapy plan information such as a tumor region, irradiation region, and irradiation method by using a three-dimensional medical image.

Figure 4:
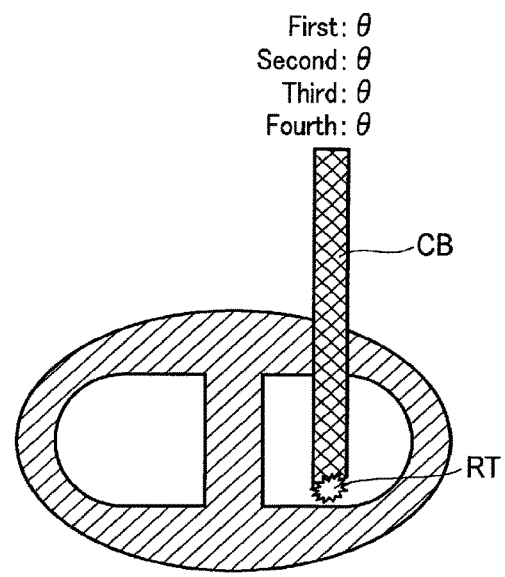
FIG. 4 is a view for explaining the initial irradiation directions calculated by the processing circuitry in step S4 in FIG. 3.

FIG. 4 is a view for explaining the initial irradiation directions calculated by the processing circuitry 71 in step S4. The processing circuitry 71 calculates the initial irradiation directions of particle beams corresponding to a predetermined count, which irradiate at almost the same position, that is a tumor region RT, in the same direction. More specifically, as shown in FIG. 4, the irradiation directions of particle beams are set to pass through the tumor region RT. That is, for example, as shown in FIG. 4, when the repetitive irradiation count of each field in repainting is four, all the irradiation directions (irradiation angles) of four particle beam irradiations are set to θ. The irradiation angle θ is the rotation angle of a particle beam radiation head. It is preferable to calculate the irradiation direction θ based on radiotherapy plan information such as a tumor region, irradiation region, and irradiation method. Although FIG. 4 shows only one irradiation direction as number of beams for the sake of simplicity, two to four suitable irradiation directions angles are usually selected.

As shown in FIG. 4, upon calculating initial irradiation directions, the processing circuitry 71 calculates an initial dose distribution based on the initial irradiation directions. In this operation example, the processing circuitry 71 calculates a dose distribution so as to form a Spread-out Bragg peak in a tumor region. It is possible to spread out a Bragg peak by applying particle beams in the same irradiation direction while changing the Bragg peak position of each particle beam along a depth direction.

Note that in this embodiment, it is possible to calculate initial irradiation directions and an irradiation dose based on an expected dose distribution as well as calculating an initial dose distribution based on the initial irradiation directions. For example, the processing circuitry 71 sets a dose distribution (a dose in a tumor region and the upper limit of the dose on a risk organ) expected by the user, and selects an irradiation direction and an irradiation dose in accordance with the set dose distribution.

Upon determining that the doses on normal tissues are high through after observation of the initial dose distribution calculated in step S4, the processing circuitry 71 stands ready to issue an instruction to disperse irradiation directions via the input circuitry 75 (step S5).

Figure 5:
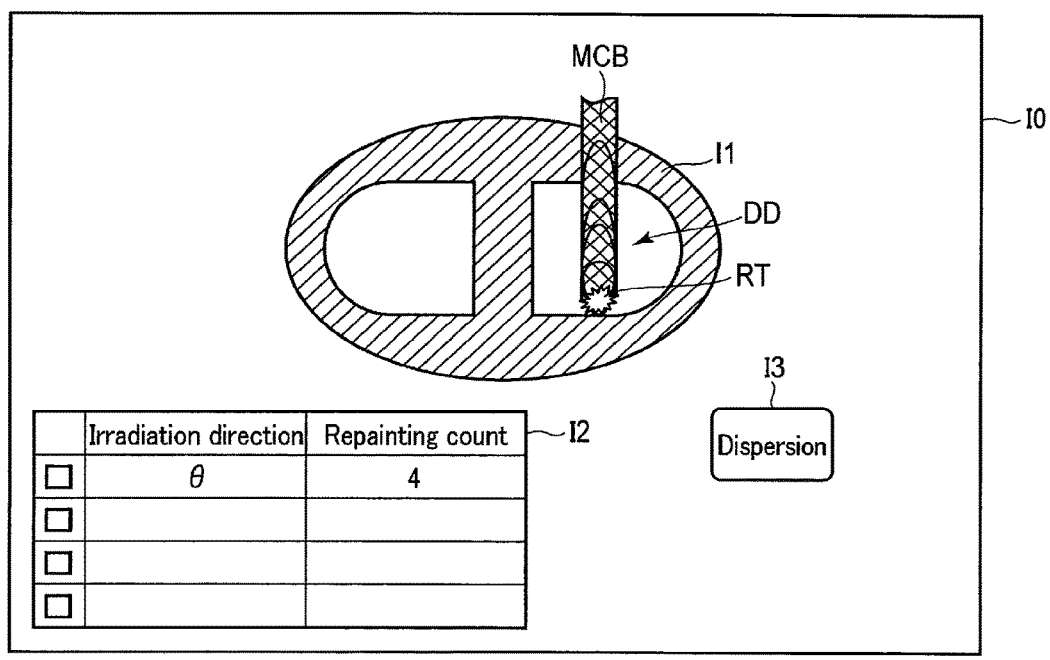
FIG. 5 is a view showing an example of a display screen of the initial irradiation directions and the initial dose distribution displayed by display circuitry in step S5 in FIG. 3.

FIG. 5 shows an example of a display screen I0 for an initial irradiation direction and an initial dose distribution displayed by the display circuitry 74 in step S4. As shown in FIG. 5, the display screen I0 displays a medical image I1 including the tumor region RT. The medical image I1 is, for example, an MPR image including the RT which is generated by applying MPR processing to a three-dimensional medical image using the image processing circuitry 72. The tumor region RT, a risk organ and lines DD representing the initial dose distribution are superimposed on the medical image I1. The display screen I0 also displays a display column 12 indicating the irradiation direction of each field and a repetitive irradiation count (repainting count). An irradiation direction is represented by an irradiation angle.

As shown in FIG. 5, the display screen I0 further displays a dispersion instruction button I3. The dispersion instruction button I3 is a button for issuing an instruction to disperse irradiation directions. A user such as a doctor observes the lines DD displayed on the display screen I0, and evaluates the validity of the initial dose distribution. The properties of proton beams and heavy-ion beams will be described below.

Figure 6:
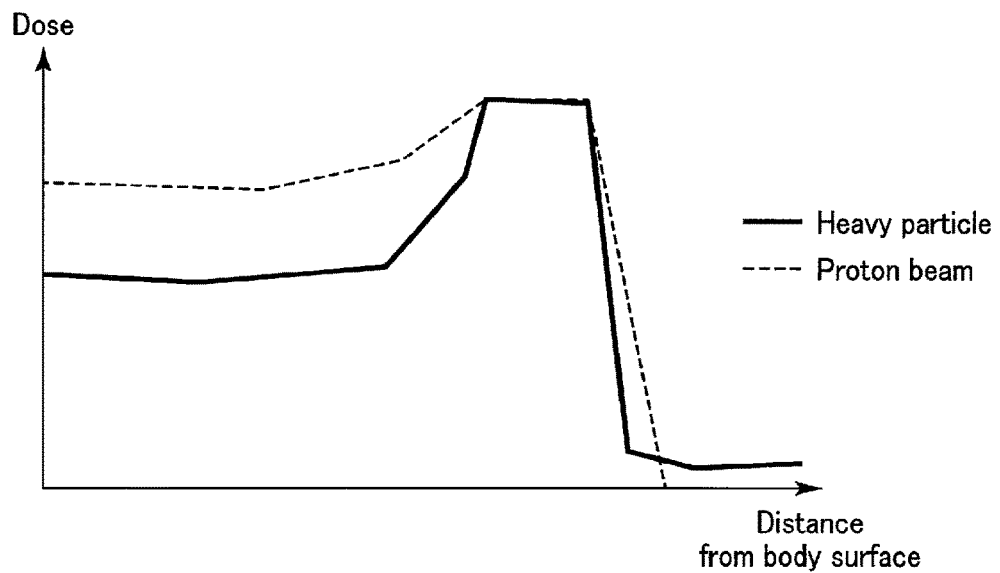
FIG. 6 is a graph showing the Spread-out Bragg peak dose distributions of proton beams and heavy particle beams.

FIG. 6 is a graph showing the Spread-out Bragg peak dose distributions of proton beams and heavy-ion beams. Referring to FIG. 6, the ordinate represents dose, and the abscissa represents distance from the body surface. As shown in FIG. 6, a Spread-out Bragg peak is formed by applying particle beams in the same irradiation direction while changing the Bragg peaks position in each particle beam along a depth direction. As indicated by the dotted line in FIG. 6, the proton beams hardly provide any dose to a portion deeper than the range. In addition, the proton beams provide larger doses to a portion shallower than the range than heavy-ion beams. When a Spread-out Bragg peak is formed by using proton beams, the dose on the front side of a target tumor sometimes reaches 80% of the peak. Heavy-ion beams provide smaller doses to a portion shallower than the range than proton beams, but also provide slight doses to even a portion deeper than the range. When a Spread-out Bragg peak is to be formed by using heavy-ion beams, it should be noted that doses also leak out to the rear side of the peak.

When forming a Spread-out Bragg peak using particle beams, a user such as a doctor pays attention to whether sufficient doses can be distributed to the tumor region RT and the doses on normal tissues, especially the risk organ and the skin are higher than necessary. Upon determining that the initial dose distribution poses a risk, the user presses the dispersion instruction button I3 via the input circuitry 75.

In response to the pressing of the dispersion instruction button I3 (YES in step S5), the processing circuitry 71 executes the direction dispersion function 715 (step S6). In step S6, the processing circuitry 71 disperses the same initial irradiation directions of the respective fields to different irradiation directions in response to the issuance of a dispersion instruction via the input circuitry 75.

Figure 7:
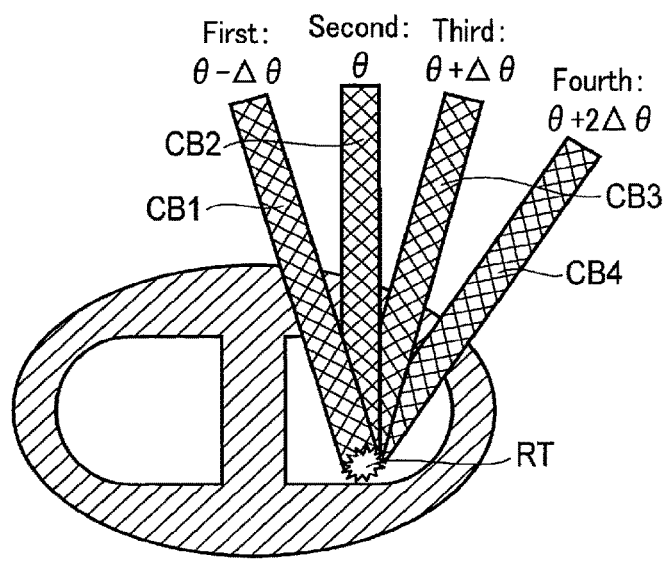
FIG. 7 is a view for explaining direction dispersion processing for irradiation directions by the processing circuitry in step S6.

FIG. 7 is a view for explaining the direction dispersion function 715 for irradiation directions executed by the processing circuitry 71 in step S6. The processing circuitry 71 disperses the initial irradiation directions of a predetermined count of irradiation in the same direction toward almost the same position. The dispersed irradiation directions of the predetermined count separate from each other by a predetermined angle $\Delta\theta$.

The dispersed irradiation directions are set, centered at the same position, so as to separate from each other by the predetermined angle $\Delta\theta$. More specifically, as shown in FIG. 7, the processing circuitry 71 arranges the initial irradiation directions, set in the same direction throughout the repetitive irradiation count (repainting count), at predetermined angular intervals $\Delta\theta$. Assume that the repetitive irradiation count of each field in multi-field irradiation is four, the irradiation direction (rotation angle) of the first field is $\theta$, and the irradiation direction (rotation angle) of the second field is $\phi$. In this case, when all the irradiation directions of the first to fourth irradiations from the first field are $\theta°$, the processing circuitry 71 changes the irradiation direction of the first particle beam irradiation to $\theta-\Delta\theta°$, the irradiation direction of the second particle beam irradiation to $\theta°$, the irradiation direction of the third particle beam irradiation to $\theta+\Delta\theta°$, and the irradiation direction of the fourth particle beam irradiation to $\theta+2\Delta\theta°$.

Likewise, when all the irradiation directions of the first to fourth irradiations from the second field are $\phi°$, the processing circuitry 71 changes the irradiation direction of the first particle beam irradiation to $\phi-\Delta\phi°$, the irradiation direction of the second particle beam irradiation to $\phi°$, the irradiation direction of the third particle beam irradiation to $\phi+\Delta\phi°$, and the irradiation direction of the fourth particle beam irradiation to $\phi+2\Delta\phi°$. In this case, the angular intervals $\Delta\theta$ and $\Delta\phi$ are set to the same value. The angular intervals $\Delta\theta$ and $\Delta\phi$ may be registered in advance. Alternatively, the user may set the angular intervals $\Delta\theta$ and $\Delta\phi$ to arbitrary values via the input circuitry 75. In this case, when the user presses an angle changing button of the GUI displayed on the display screen via the input circuitry 75, the processing circuitry 71 may accept changes in the angular intervals $\Delta\theta$ and $\Delta\phi$.

The angular intervals $\Delta\theta$ and $\Delta\phi$ are set to angles smaller than the angle between the adjacent fields. If the angular intervals $\Delta\theta$ and $\Delta\phi$ are large like the angle between the adjacent fields, radiotherapy planning needs to be executed again. For this reason, the angular intervals are set in the above manner to avoid such re-planning.

Note that the angular intervals may be changed depending on whether PBS or BBS is used. More specifically, in the case of BBS, a bolus (absorber) conforming to the shape of a tumor is required. It is not practical to form such a bolus for each irradiation direction for the dispersion of irradiation directions. For this reason, in the case of BBS, angular intervals are set within a range in which changes in irradiation direction can be almost neglected (for example, 0.5° or 1°). In contrast to this, PBS is free from such restrictions, and angular intervals of 2° to 5° are thought to be appropriate.

In addition, the angular intervals $\Delta\theta$ and $\Delta\phi$ may be individually set in accordance with the size of a tumor region. For example, the processing circuitry 71 preferably uses a look up table (to be referred to as an angle table hereinafter) associating angular intervals with the sizes of tumor regions. The angle table is stored in, for example, the storage circuitry 76. The size of a tumor region is defined by the volume, diameter, radius, or the like of the tumor region. Typically, an angle is decided so as to set a larger angular interval with an increase in the size of a tumor region. In this case, the processing circuitry 71 measures the size of the tumor region identified in step S1, searches the angle table by using the measured size as a key, and specifies an angular interval associated with the size by the angle table, thereby setting the specified angular interval as a set angular interval. This allows the processing circuitry 71 to automatically set an angular interval suitable for the size of a tumor region.

In addition, an angular interval may be decided in consideration of the directivity of the size of a tumor region. That is, an angular interval may be decided in accordance with the size of a tumor region in a direction almost parallel to the irradiation direction of a particle beam or may be decided in accordance with the size of a tumor region in a direction almost perpendicular to the irradiation direction of a particle beam and almost parallel to the rotating direction of the gantry of the radiotherapy apparatus.

Figure 8:
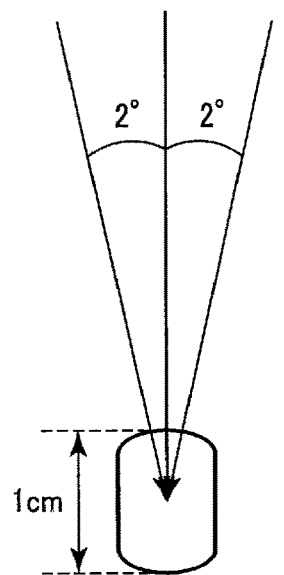
FIG. 8 is a view showing the relationship between angular intervals and the size of a tumor region in the depth direction according to this embodiment.
Figure 9:
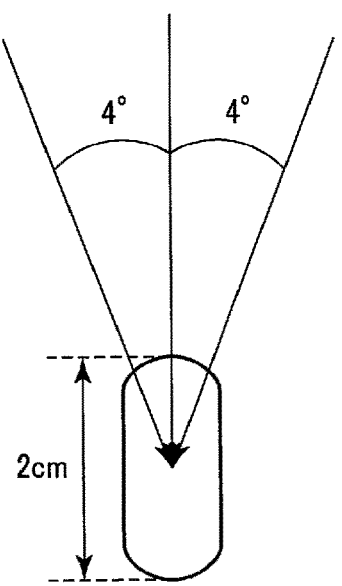
FIG. 9 is another view showing the relationship between angular intervals and the size of a tumor region in the depth direction according to this embodiment.

FIGS. 8 and 9 are views each showing the relationship between angular intervals and the size of a tumor region in a direction (to be referred to as a depth direction hereinafter) almost parallel to the irradiation direction of a particle beam. As indicated by the comparison between FIGS. 8 and 9, a larger angular interval is preferably set with an increase in the length of a tumor region in the depth direction. For example, as shown in FIG. 8, when the length of the tumor region in the depth direction is 1 cm, the angular interval is 2°. As shown in FIG. 9, when the length of the tumor region in the depth direction is 2 cm, the angular interval is preferably set to 4°, which is larger than 2°. In order to distribute particle beams so as to cover a tumor region long in the depth direction, the peak width of the Spread-out Bragg peak needs to be increased. However, forming a Spread-out Bragg peak having a large peak width will make doses concentrate at even shallower positions. Increasing an angular interval with an increase in the size of a tumor region in the depth direction can avoid such concentration of doses.

FIGS. 10 and 11 are views each showing the relationship between angular intervals and the size of a tumor region in a direction (to be referred to as a rotating direction hereinafter) almost perpendicular to the irradiation direction of a particle beam and almost parallel to the rotating direction of the gantry of the radiotherapy apparatus. As indicated by the comparison between FIGS. 10 and 11, a larger angular interval is preferably set with an increase in the length of a tumor region in the rotating direction. For example, as shown in FIG. 10, when the length of the tumor region in the rotating direction is 1 cm, the angular interval is 2°. As shown in FIG. 11, when the length of the tumor region in the rotating direction is 2 cm, the angular interval is preferably set to 4°, which is larger than 2°. In order to irradiate the entire tumor region with particle beams, a particle beam needs to be applied a larger number of times with an increase in the size of the tumor region in the rotating direction. Because particle beams are applied in almost the same irradiation direction, applying a particle beam a large number of times tends to make doses concentrate at shallow positions, especially the skin. It is possible to reduce such dose concentration by increasing an angular interval with an increase in the size of a tumor region in the rotating direction.

Upon executing step S6, the processing circuitry 71 executes the dose modification function 716 (step S7). In step S7, the processing circuitry 71 modifies the dose distribution calculated by the initial direction/dose calculation function 714 based on a plurality of dispersed irradiation directions. The display circuitry 74 preferably displays also the modified dose distribution. This allows the user to determine the validity of the modified dose distribution.

Upon determining that the modified dose distribution is valid, the processing circuitry 71 determines the modified dose distribution, the modified irradiation directions, the tumor region, the irradiation region, and the irradiation method as radiotherapy plan information. The radiotherapy plan information is supplied to the radiotherapy information system 8 or the radiotherapy apparatus 9 to be used for radiotherapy.

The above concludes the description of radiotherapy planning implemented by causing the processing circuitry 71 to execute the radiotherapy planning program.

As described above, according to this operation example, it is possible to avoid the concentration of doses on normal tissues and the like by dispersing the irradiation directions of the respective particle beam irradiations in repainting as compared with the case in which particle beams are applied in the same direction. This makes it possible to more safely perform radiotherapy using particle beams.

Note that in the above operation example, a dispersion instruction is issued with respect to all the fields (irradiation directions). However, this embodiment is not limited to this. For example, an irradiation direction as a dispersion instruction target may be selected with respect to a specific field in accordance with an instruction issued by the user via the input circuitry 75. The manner of selecting a field as a dispersion instruction target will be described below.

Figures 12, 13:
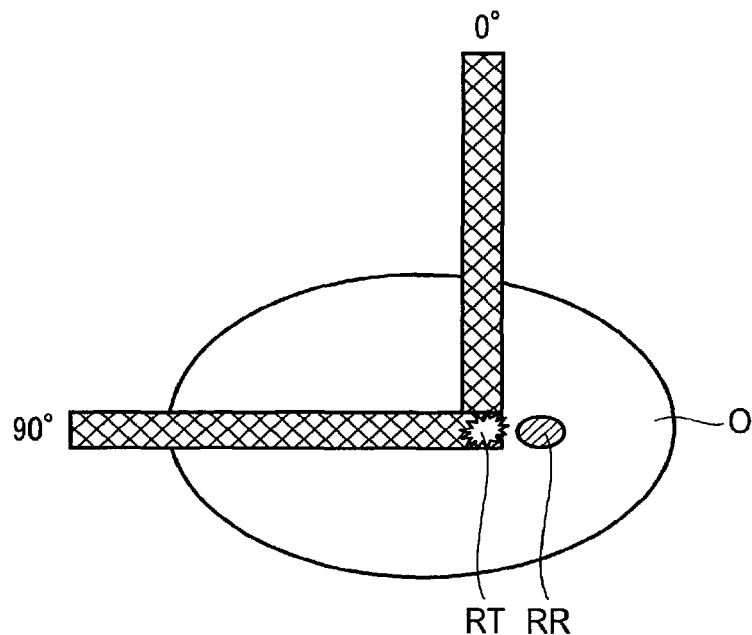
FIG. 12 is a view showing a typical example of selecting a field as a dispersion instruction target according to this embodiment.
FIG. 13 is a view showing an example of a method of selecting a field as a dispersion instruction target according to this embodiment.

FIG. 12 shows a typical example of selecting a field as a dispersion instruction target. As shown in FIG. 12, consider a case in which the initial number of beams is 2, and particle beam irradiation is performed in two directions, namely irradiation directions 0° and 90°. Assume that a tumor RT and a risk organ RR exist in the body of a patient O, and the risk organ RR is positioned on the deep side of the tumor RT in the depth direction of a particle beam in irradiation direction 90°. In this case, in irradiation direction 90°, the effect of the Bragg peak prevents any particle beam from reaching the deep side of the tumor RT, thus eliminating the risk of causing any particle beam from reaching the risk organ RR. Accordingly, no problem arises even when a dispersion instruction is issued with respect to irradiation direction 90°. However, in irradiation direction 0°, the risk organ RR is positioned adjacent to the tumor RT in the rotating direction. Accordingly, issuing a dispersion instruction with respect to irradiation direction 0° may cause irradiation of the risk organ RR with particle beams. It is therefore preferable to exclude irradiation direction 0° from dispersion instruction targets, in which the issuance of a dispersion instruction will increase the risk of irradiating the risk organ RR with particle beams.

FIG. 13 shows an example of a method of selecting a field as a dispersion instruction target. As shown in FIG. 13, when multi-field irradiation is scheduled, the display column I2 displays a list of checkboxes C1, irradiation directions, and repainting counts corresponding to the respective fields. In the example shown in FIG. 12, for example, irradiation direction 0° and irradiation direction 90° are displayed. The user checks, via the input circuitry 75, the checkbox C1 corresponding to a field to which a dispersion instruction is issued. In the example shown in FIG. 12, the user checks the checkbox C1 corresponding to irradiation direction 90° because there is no risk of distributing any particle beam to the risk organ by direction dispersion in this direction, but does not check the checkbox C1 corresponding to irradiation direction 0° because there is a risk of distributing particle beams to the risk organ. The processing circuitry 71 can perform the above irradiation direction dispersion with respect to only the field corresponding to the checked checkbox. This allows the processing circuitry 71 to perform irradiation direction dispersion with respect to only the fields free from the above risk.

Modification

In the above embodiment, the radiotherapy planning apparatus 7 executes radiotherapy planning. However, this embodiment is not limited to this. In a modification, the radiotherapy apparatus 9 executes radiotherapy planning. The radiotherapy apparatus 9 according to this modification will be described below. Note that in the following description, the same reference numerals denote constituent elements having almost the same functions as those included in this embodiment, and a repetitive description will be made only when required.

FIG. 14 is a block diagram showing the arrangement of the radiotherapy apparatus 9 according to the modification of this embodiment. As shown in FIG. 14, the radiotherapy apparatus 9 includes processing circuitry 91, image processing circuitry 92, communication circuitry 93, display circuitry 94, input circuitry 95, storage circuitry 96, control circuitry 97, acceleration system control circuitry 971, irradiation system control circuitry 973, motor control circuitry 975, an accelerator 981, a transport system 982, and a gantry 99. The processing circuitry 91, the image processing circuitry 92, the communication circuitry 93, the display circuitry 94, the input circuitry 95, the storage circuitry 96, and the control circuitry 97 are communicatively connected to each other.

The processing circuitry 91 includes, as hardware resources, a processor such as a CPU or GPU and memories such as a ROM and a RAM. Like the processing circuitry 71 of the radiotherapy planning apparatus 7 in FIG. 2, the processing circuitry 91 executes the tumor identifying function 711, the irradiation region decision function 712, the irradiation method selection function 713, the initial direction/dose calculation function 714, the direction dispersion function 715, and the dose modification function 716 when executing radiotherapy planning. A description of the functions 711, 712, 713, 714, 715, and 716 will be omitted to avoid redundancy.

The image processing circuitry 92 includes, as hardware resources, a processor such as a CPU, GPU, MPU and memories such as a ROM and a RAM. The image processing circuitry 92 applies various types of image processing to three-dimensional medical images. For example, the image processing circuitry 92 generates two-dimensional medical images for display by applying three-dimensional medical image processing such as volume rendering, surface volume rendering, image value projection processing, MPR processing, and CPR processing to three-dimensional medical images. Note that the image processing circuitry 92 may be implemented by an ASIC, FPGA, CPLD, or SPLD which can implement the above image processing.

The communication circuitry 93 performs data communication with the PET apparatus 1, the SPECT apparatus 2, the X-ray computed tomography apparatus 3, the magnetic resonance imaging apparatus 4, the X-ray angiography apparatus 5, the PACS 6, the radiotherapy planning apparatus 7, and the radiotherapy information system 8, which constitute the radiotherapy system 100, via a wired or wireless means (not shown).

The display circuitry 94 displays display screens and medical images for radiotherapy planning. More specifically, the display circuitry 94 includes a display interface and a display device. The display interface converts data representing a display target into a video signal. The video image is supplied to the display device. The display device displays the video signal representing the display target. As a display device, it is possible to use, for example, a CRT display, liquid crystal display, organic EL display, LED display, plasma display, or arbitrary display known in this technical field.

More specifically, the input circuitry 95 includes an input device and an input interface. The input device accepts various types of commands from the user. As input devices, it is possible to use a keyboard, mouse, various types of switches, and the like. The input interface supplies output signals from the input device to the processing circuitry 91, the image processing circuitry 92, and the control circuitry 97 via a bus.

The storage circuitry 96 is a storage such as an HDD, SSD, or integrated circuit storage which stores various types of information. Alternatively, the storage circuitry 96 may be a drive assembly or the like which reads and writes various types of information from and to portable storage media such as a CD-ROM drive, DVD drive, and flash memory.

The accelerator 981 generates particle beams by accelerating heavy-ions, protons, or the like generated by an ion source or the like by using a linear accelerator, circular accelerator, or the like. The acceleration system control circuitry 971 controls the accelerator 981. The transport system 982 is a transport path for transporting the particle beam exiting from the accelerator 981 to the gantry 99. The gantry 99 includes a rotating portion 991 and a fixed portion 992. The fixed portion 992 is installed on the floor surface and supports the rotating portion 991 so as to allow it to rotate about the rotation axis. A radiation head 993 is attached to the rotating portion 991. The radiation head 993 irradiates the patient O placed on a bed 995 with the particle beams transported by the transport system 982. The radiation head 993 is equipped with an optical sight such as a multileaf collimator, and can form a particle beam in conformity with the shape of an irradiation region. The radiation head 993 has an electromagnetic deflecting plate for deflection in a lateral direction and an electromagnetic deflecting plate for deflection in a longitudinal direction. Note that the lateral direction coincides with the rotating direction of the rotating portion 991, and the longitudinal direction is perpendicular to the lateral direction. The motor 994 is incorporated in the fixed portion 992. A motor 994 generates a motive power for allowing the fixed portion 992 to rotate the rotating portion 991. Motor control circuitry 975 controls the motor 994. The motor control circuitry 975 drives the motor 994 to place the radiation head 993 at a predetermined rotation angle.

The control circuitry 97 functions as the main unit of the radiotherapy apparatus 9. The control circuitry 97 controls the acceleration system control circuitry 971, the irradiation system control circuitry 973, and the motor control circuitry 975 in accordance with the radiotherapy plan information generated by the processing circuitry 71 or 91 or the like, thereby irradiating the patient O with particle beams. More specifically, the control circuitry 97 controls the acceleration system control circuitry 971, the irradiation system control circuitry 973, and the motor control circuitry 975 to implement the dose distribution decided by the processing circuitry 71 or 91 or the like in accordance with scheduled irradiation directions and a scheduled irradiation method. More specifically, the motor control circuitry 975 controls the motor 994 to place the radiation head 993 at the rotation angle θ of each field and dispersed angles. Dispersing the irradiation directions of the respective particle beam irradiations in repainting can avoid the concentration of doses on a normal tissue or the like.

Note that the apparatus to be used to execute radiotherapy planning is not limited to the radiotherapy planning apparatus 7 or the radiotherapy apparatus 9. For example, it is possible to execute a radiotherapy plan by installing a radiotherapy planning program in the radiotherapy information system 8 and causing the tumor identifying function 711, the irradiation region decision function 712, the irradiation method selection function 713, the initial direction/dose calculation function 714, the direction dispersion function 715, and the dose modification function 716 to execute the program.

Review

As has been described above, the radiotherapy planning apparatus 7, the radiotherapy information system 8, and the radiotherapy apparatus 9 according to this embodiment each include the processing circuitry 71 or 91. The processing circuitry 71 or 91 includes at least the initial direction/dose calculation function 714, the direction dispersion function 715, and the dose modification function 716. The initial direction/dose calculation function 714 calculates the initial irradiation directions of particle beams and a dose distribution corresponding to the initial irradiation directions by using a three-dimensional medical image concerning an object. The direction dispersion function 715 disperses some or all of the initial irradiation directions in response to the issuance of a dispersion instruction via the input device. The dose modification function 716 modifies the dose distribution based on the dispersed irradiation directions.

The above arrangement makes it possible to disperse the irradiation directions of particle beams if there is a risk in the initial dose distribution. This can avoid the concentration of doses on a normal tissue, and hence allows safe radiotherapy with particle beams.

According to this embodiment, therefore, it is possible to avoid an increase in dose on a normal tissue.

While certain embodiments have been described, these embodiments have been presented by way of example only, and are not intended to limit the scope of the inventions. Indeed, the novel embodiments described herein may be embodied in a variety of other forms; furthermore, various omissions, substitutions and changes in the form of the embodiments described herein may be made without departing from the spirit of the inventions. The accompanying claims and their equivalents are intended to cover such forms or modifications as would fall within the scope and spirit of the inventions.

The invention claimed is:

1. A radiotherapy planning apparatus, comprising:
processing circuitry;
a display apparatus coupled to the processing circuitry;
an input device, coupled to the processing circuitry, configured to receive input instructions from a user and forward the input instructions to the processing circuitry; and
a memory to store a plurality of angles in association with a plurality of tumor region sizes,
wherein the processing circuitry is configured to:
calculate, by using a three-dimensional medical image concerning an object, an initial irradiation directions of multiple particle beams to be used to irradiate a tumor region and an initial dose distribution provided by the multiple particle beams, the initial irradiation directions of the multiple particle beams facing a same initial direction, and an angle between the multiple particle beams being zero;
generate first image data representing the initial irradiation directions and the initial dose distribution with reference to an acquired medical image of the tumor region and a risk organ in the object and output the first image data to the display apparatus;
select a specified angle from the plurality of angles stored in the memory, based on a size of the tumor region, each of the stored plurality of angles being a spread angle between pairs of adjacent beams of the multiple particle beams after a dispersion process;
modify the initial dose distribution by performing the dispersion process on the initial irradiation directions in response to a dispersion instruction issued by the user via the input device, the dispersion process generating dispersed irradiation directions for irradiation of the multiple particle beams by changing the initial irradiation directions so that the pairs of the adjacent beams are separated from each other by the specified angle;
calculate a modified dose distribution based on the multiple particle beams to be used to irradiate in the dispersed irradiation directions;
generate second image data representing the modified dose distribution with reference to the medical image of the tumor region and the risk organ and output the second image data to the display apparatus; and
transmit, to control circuitry of a radiation therapy apparatus that includes a radiation head, information of the dispersed irradiation directions and the modified dose distributions, the control circuitry controlling the radiation head to irradiate the multiple particle beams, in response to receiving the information of the dispersed irradiation directions and the modified dose distribution, to perform radiotherapy of the tumor region.

2. The radiotherapy planning apparatus of claim 1, wherein the processing circuitry is further configured to calculate the initial irradiation directions such that a particle beam is expected to be used to irradiate the tumor region a predetermined number of times in the initial direction as the multiple particle beams.

3. The radiotherapy planning apparatus of claim 2, wherein the predetermined number of times is not more than five.

4. The radiotherapy planning apparatus of claim 1, wherein the processing circuitry is further configured to:
calculate the initial irradiation directions and the initial dose distribution so that the multiple particle beams to be irradiated in an identical initial irradiation direction toward the tumor region are expected to form a spread-out Bragg peak at the tumor region by providing different Bragg peak positions along the initial irradiation directions; and
modify the initial dose distribution by dispersing the initial irradiation directions in order to reduce dose to be provided by the multiple particle beams to a shallower position along the initial irradiation directions than a position where the spread-out Bragg peak is formed.

5. The radiotherapy planning apparatus of claim 1, wherein the predetermined angle is not more than 5°.

6. The radiotherapy planning apparatus of claim 1, wherein the processing circuitry is further configured to select the specified angle by reading out, from the memory, one of the plurality of angles based on the size of the tumor region, which is defined as a length of the tumor region taken in an irradiation direction of a particle beam.

7. The radiotherapy planning apparatus of claim 1, wherein the processing circuitry is further configured to select the specified angle by reading out, from the memory, one of the plurality of angles based on the size of the tumor region, which is defined as a length of the tumor region taken in a direction parallel to a rotating direction of a gantry of a radiotherapy apparatus.

8. The radiotherapy planning apparatus of claim 1, wherein the specified angle is further designated by a user via the input device.

9. The radiotherapy planning apparatus of claim 1, wherein
the processing circuitry is further configured to calculate the initial irradiation directions of the multiple particle beams to be used to irradiate the tumor region and initial dose distributions provided by the multiple particle beams to be used to irradiate in the initial irradiation directions by using the three dimensional medical image concerning the object, and
the initial irradiation directions to be dispersed by the processing circuitry are designated by the user via the input device.

10. The radiotherapy planning apparatus according to claim 1, wherein the processing circuitry is further configured to
calculate the initial irradiation directions of the multiple particle beams to be used to irradiate the tumor region and the initial dose distribution provided by the multiple particle beams to be used to irradiate in the initial irradiation directions by using the three-dimensional medical image concerning the object, and
disperse the initial irradiation directions in response to the dispersion instruction issued by the user via the input device.

11. The radiotherapy planning apparatus according to claim 1, wherein
the processing circuitry is further configured to selectively operate in a broad beam scan mode or a pencil beam scan mode, the broad beam scan mode being for planning to use a first particle beam which is formed in conformity with a shape of an irradiation target region, the pencil beam scan mode being for planning to use a second particle beam which is formed into a thinner shape than the first particle beam so that repeated irradiation of the second particle beam is necessary to irradiate an entirety of the irradiation target region.

12. The radiotherapy planning apparatus of claim 1, wherein the size of the tumor region is defined as a length of the tumor region taken in the initial direction.

13. The radiotherapy planning apparatus of claim 1, wherein the multiple particle beams are either proton beams or heavy-ion beams.

14. The radiotherapy planning apparatus of claim 1, wherein the processing circuitry is further configured to generate radiotherapy plan information to be used for radiotherapy when the processing circuitry is notified by the user via the input device that the modified dose distribution is valid, the radiotherapy plan information including the dispersed irradiation directions and the modified dose distribution,
wherein the display apparatus is configured to display, for review by the user, a first screen image representing the initial dose distribution based on the first image data and a second screen image representing the modified dose distribution based on the second image data.

15. A radiotherapy apparatus, comprising:
processing circuitry;
a display apparatus coupled to the processing circuitry;
an input device coupled to the processing circuitry for a user to input instructions to the processing circuitry;
a memory to store a plurality of angles in association with a plurality of tumor region sizes;
a radiation head configured to radiate a particle beam; and
control circuitry configured to control the radiation head,
wherein the processing circuitry is configured to
calculate, by using a three-dimensional medical image concerning an object, initial irradiation directions of multiple particle beams to be used to irradiate a tumor region and an initial dose distribution provided by the multiple beams, the initial irradiation directions of the multiple particle beams facing a same initial direction, and an angle between the multiple particle beams being zero;
generate first image data representing the initial irradiation directions and the initial dose distribution with reference to an acquired medical image of the tumor region and a risk organ in the object and output the first image data to the display apparatus;
select a specified angle from the plurality of angles stored in the memory, based on a size of the tumor region, each of the stored plurality of angles being a spread angle between pairs of adjacent beams of the multiple particle beams after a dispersion process;
modify the initial dose distribution by performing the dispersion process on the initial irradiation directions in response to a dispersion instruction issued by the user via the input device, the dispersion process generating dispersed irradiation directions of the multiple particle beams by changing the initial irradiation directions so that the pairs of the adjacent beams are separated from each other by the specified angle;
calculate a modified dose distribution based on the multiple particle beams to be used to irradiate in the dispersed irradiation directions; and
generate second image data representing the modified dose distribution with reference to the medical image of the tumor region and the risk organ and output the second image data to the display apparatus; and
wherein the control circuitry is further configured to control the radiation head to irradiate the multiple particle beams in the dispersed irradiation directions using the modified dose distribution to perform radiotherapy of the tumor region.

16. The radiotherapy apparatus according to claim 15, wherein the processing circuitry is further configured to
calculate the initial irradiation directions of the multiple particle beams to be used to irradiate the tumor region and the initial dose distribution provided by the multiple particle beams to be used to irradiate in the initial irradiation directions by using the three-dimensional medical image concerning the object, and
disperse the initial irradiation directions in response to the dispersion instruction issued by the user via the input device.

17. The radiotherapy apparatus according to claim 15, wherein
the processing circuitry is further configured to selectively operate in a broad beam scan mode or a pencil beam scan mode, the broad beam scan mode being for planning to use a first particle beam which is formed in conformity with a shape of an irradiation target region, the pencil beam scan mode being for planning to use a second particle beam which is formed into a thinner shape than the first particle beam so that repeated irradiation of the second particle beam is necessary to irradiate an entirety of the irradiation target region.

18. The radiotherapy apparatus of claim 15, wherein the size of the tumor region is defined as a length of the tumor region taken in the initial direction.

19. The radiotherapy apparatus of claim 15, wherein the multiple particle beams are either proton beams or heavy-ion beams.

20. A radiotherapy planning method, comprising:
storing, in a memory, a plurality of angles in association with a plurality of tumor region sizes;
causing processing circuitry to calculate, by using a three-dimensional medical image concerning an object, initial irradiation directions of multiple particle beams to be irradiated to a tumor region and an initial dose distribution provided by the multiple particle beams, the initial irradiation directions of the multiple particle beams facing a same initial direction, and an angle between the multiple particle beams being zero;
causing the processing circuitry to generate first image data representing the initial irradiation directions and the initial dose distribution with reference to an acquired medical image of the tumor region and a risk organ in the object and output the first image data to a display apparatus;
selecting a specified angle from the plurality of angles stored in the memory, based on a size of the tumor region, each of the stored plurality of angles being a spread angle between pairs of adjacent beams of the multiple particle beams after a dispersion process;
causing the processing circuitry to modify the initial dose distribution by performing the dispersion process on the initial irradiation directions in response to a dispersion instruction issued by a user via an input device, the dispersion process generating dispersed irradiation directions of the multiple particle beams by changing the initial irradiation directions so that the pairs of the adjacent beams are separated from each other by the specified angle;
causing the processing circuitry to calculate a modified dose distribution based on the multiple particle beams to be used to irradiate in the dispersed irradiation directions;
causing the processing circuitry to generate second image data representing the modified dose distribution with reference to the medical image of the tumor region and the risk organ and output the second image data to the display apparatus; and
controlling a radiation head of a radiotherapy apparatus to irradiate the multiple particle beams in the dispersed irradiation directions using the modified dose distribution to perform radiotherapy of the tumor region.

21. The radiotherapy planning method according to claim 20, further comprising causing the processing circuitry to
calculate the initial irradiation directions of the multiple particle beams to be irradiated to the tumor region and the initial dose distribution provided by the multiple particle beams to be used to irradiate in the initial irradiation directions by using the three-dimensional medical image concerning the object, and
disperse the initial irradiation directions in response to the dispersion instruction issued by the user via the input device.

22. The radiotherapy planning method according to claim 20, further comprising
causing the processing circuitry to selectively operate in a broad beam scan mode or a pencil beam scan mode, the broad beam scan mode being for planning to use a first particle beam which is formed in conformity with a shape of an irradiation target region, the pencil beam scan mode being for planning to use a second particle beam which is formed into a thinner shape than the first particle beam so that repeated irradiation of the second particle beam is necessary to irradiate an entirety of the irradiation target region.

23. The radiotherapy planning method of claim 20, wherein the size of the tumor region is defined as a length of the tumor region taken in the initial direction.

24. The radiotherapy planning method of claim 20, wherein the multiple particle beams are either proton beams or heavy-ion beams.

* * * * *